United States Patent [19]

Tulok

[11] Patent Number: 5,366,723

[45] Date of Patent: Nov. 22, 1994

[54] METHOD OF ALLEVIATING TOXICITY ORIGINATING FROM TREATMENT WITH ANTICANCER PLATINUM COMPOUNDS

[76] Inventor: Istvan Tulok, 1525 Budapest PF. 21. XII,, Ráth GY. U. 7/9, Hungary

[21] Appl. No.: 27,135

[22] Filed: Mar. 5, 1993

[51] Int. Cl.$^5$ .................. A61K 49/00; A61K 33/24; A61K 31/28; A61K 31/195
[52] U.S. Cl. .................. 424/10; 424/649; 514/492; 514/561; 514/562
[58] Field of Search .................. 514/561, 562, 492; 424/10, 649

[56] References Cited

U.S. PATENT DOCUMENTS

| | | | |
|---|---|---|---|
| 4,547,377 | 10/1985 | Ogawa et al. | 426/268 |
| 5,039,704 | 8/1991 | Smith et al. | 514/563 |

FOREIGN PATENT DOCUMENTS 1-020128  4/1989  Japan .

*Primary Examiner*—Raymond J. Henley, III
*Attorney, Agent, or Firm*—Pravel, Hewitt, Kimball & Krieger

[57] ABSTRACT

The present invention concerns a method of administering the amino acids L-glutamic acid, L-aspartic acid and L-cysteine for alleviating the toxicity associated with the administration of anticancer platinum compounds such as cisplatin and its derivatives.

11 Claims, No Drawings

METHOD OF ALLEVIATING TOXICITY ORIGINATING FROM TREATMENT WITH ANTICANCER PLATINUM COMPOUNDS

SPECIFICATION

The present invention concerns a new biochemical modulator which mitigates or eliminates the toxic side effects of cytotoxic agents.

In recent years intensive clinical and experimental studies have pointed out that metabolic changes and disorders accompanying different antitumor treatment modalities are to be corrected.

Damaged renal and liver functions and toxicity of bone marrow and intestinal mucosa as well as immune and vitamin deficient states and other pathological conditions without adequate compensation lead to the exhaustion of the physiological reserves of the organism and to long term or even irreversible damages of organs or organ systems.

Clinical practice has evidenced that chemotherapy and other antitumor treatments are not really effective without metabolic compensation since the malignant disease involves complex biochemical disorders. The tumor processes and antitumor interventions are associated with several "nonspecific" changes as well, which, influence the outcome of the disease.

Due to the extended screenings and results of early tumor detection, the number of patients receiving antitumor treatments keeps increasing. Nonetheless, the "molecular dietetic" correction, i.e. application of physiological substrates of metabolic disorders accompanying not only the disease itself but its treatment too, is still a pressing necessity to be solved.

Worldwide efforts are experienced to find biologically active agents able to protect the organism against the consequences of intermediary metabolic disturbances, overthrow of acid-base equilibrium and able to enhance at the same time the defensive capacity of the organism. In fact, it is a very difficult task to discover and produce such agents.

It is an object of the present invention to provide a biochemical modulator which meets these criteria.

The biochemical modulator according to the present invention consists of a composition of the amino acids L-glutamic acid, L-aspartic acid and L-cysteine. Preferably the composition is administered in the form of a tablet comprising the amino acids in the following molar ratios:

L-glutamic acid: L-cysteine from 4:1 to 1:1
L-aspartic acid: L-cysteine from 2:1 to 1:2
L-glutamic acid: L-aspartic acid from 3:1 to 1:3 or a composition containing the following components in the designated amounts (w/w):

| | |
|---|---|
| 50–60% | L-glutamic acid |
| 25–30% | L-aspartic acid |
| 15–20% | L-cysteine. |

Specifically it has been found that beneficial effect of a composition according to the invention occur in connection with the cytostatic agent Cisplatin. The fact that cisplatin and its derivatives are really potent antitumor agents is confirmed by their wide spread use in the therapy of human germ cell testicular tumors, ovarian cancers, small and non-small cell lung cancers, malignant melanoma, bladder carcinoma and certain cancers of the head and neck. It is, however, widely recognized that advances in the biochemical modulation of cisplatin toxicity should provide significant therapeutic gain for this drug in the future.

Furthermore, it is believed that the side effects of other anticancer platinum derivatives having similar mode of action as cisplatin, such as carboplatin, i.e. cis-diamine-1-1-cyclobutane dicarboxylate platinum (II)-CBDCA-, and iproplatin, i.e. cis-diisopropylamine-trans-dihydroxy-dichloro platinum (IV), -CHIP-, would be eliminated or mitigated by the composition, according to the present invention.

The amino acids glutamic acid, aspartic acid and cystein have been used previously in connection with cancer treatment. It is thus disclosed in the Japanese patent publication 89020128B that the toxicity of the anticancer agent 5-FU could be decreased if its use is combined with certain carboxylic acids or derivatives thereof. The carboxylic acids include i.a. the amino acids L-glutamic acid, L-aspartic acid and L-cysteine. It is also know that these amino acids in combination with other amino acids could be included in pharmaceutical anticancer compositions which improve the nutritional conditions, cf the Japanese Patent Publication J0 1301619. It has also been suggested that these amino acids also in combination with other amino acids can be used for transfusion in combination with cancer treatment cf. Japanese Patent Publication J 62135420-A. Thus the prior art teaches that the amino acids L-glutamic acid, L-aspartic acid and L-cysteine in combination with various other amino acids might be useful in cancer treatment. It has however never been suggested and disclosed that the combination and selection of the three amino acids according to the present invention have given good results in combination with the treatment of the anticancer agent cisplatin. The observation that the amino acid combination alleviates the side effects of cisplatin is interesting not only because of the fact that the side-effects will be less painful. It is also probable that the cisplatin dose could be increased and consequently more effective. An interesting finding contrary to what could be expected from the Japanese patent publication 89020128 is that the present combination of amino acids has not proven to be effective against 5-FU.

Our experiments were aimed at investigating the effect of Cystergin, a new chemoprotector on the bone marrow, and intestinal mucosal and kidney toxicity of cytostatics. It has been observed that the modulators of this invention, such as Cystergin, significantly reduce the kidney toxicity as proven by the significant decrease of serum creatinine, urea and gammaglutamyltranspeptidase values, which are pathologically increased during treatment of anticancer derivatives. In addition, the modulators of this invention reduce renal and liver toxicity as well as toxicity of bone marrow and intestinal mucosa. The damaging effects of cytostatics on different organs.

The damaging effects of cytostatics on different organs are well detectable under both clinical and experimental conditions. Signs, suggestive of impaired renal functions are: protein (enzymuria and elevated serum urea and creatinine) concentrations. Disturbed liver functions are reflected by elevated enzyme activity in the serum:

| | |
|---|---|
| GOT | (aspartate transferase, AST) |

| | |
|---|---|
| GPT | (alanine transferase, ALT) |
| GGT | (γ-glutamyl transpeptidase) |
| ALP | (alkaline phosphatase) |

The affected bone cells and intestinal mucosal cell show, for instance, higher alkaline phosphatase activity in the serum. Bone marrow damage is indicated by more and more anaemic state of the patient.

The following series of experiments was performed to determine the modifying effect of Cystergin on the toxicity of Cisplatin, on renal, liver and intestinal functions and on different hepatobiliary disorders.

Experimental Methods

1. Animals

Experiments were performed on H-Riop: Wistar non-inbred male rats of our own breeding. Housing conditions: Room temperature 23°–26° C.; relative humidity 40–50%; food: LATI standard rat chew, sterilized under steam, autoclaved wood shavings; 12-hour light and dark periods; no starvation before treatments; drinking water; tap water ad libitum.

Body weight of rats ranged from 180 to 200 g before the treatment. Intraperitoneal (i.p.) and oral (p.o.) treatments were given. With doses expressed in mg/kg the concentration of the active agent (i.i. Cystergin, which is an amino acid composition according to the invention) was adjusted so that the ratio of the injected volume and the animal's body weight be 1.0 ml/100 g. To the control group corresponding volumes of isotonic NaCl solution were given. Each experimental group consisted of 4 animals.

2. Treatment 2.1 Cytostatics

Cisplatin (Cis-Pt) (Platidiam, Lachema, o.p. Brno).
Cyclophosphamide (CPA) (Endoxan, Ebewe),
5-Fluorouracil (5-FU) (Hoffman La Rouche)

Animals were treated i.p. with the cytostatics dissolved in isotonic NaCl solution.

The experimental animals were killed 48 hours after the cytostatic treatment when the biochemical parameters, indicating the side effects, reached their nadir. Experiments to renal regeneration are exceptions. In this case the animals were killed at 24, 48, 74 and 96 hours after treatment respectively.

2.2 Cystergin (CR) - Composition According to the Present Invention

Preparation of the stock solution: (Active agent content of 100 tablets in 100 ml solution.) 13.3 g of l-glutamic acid, 6.6 g of L-aspartic acid were suspended in approximately 50,0 ml volume of (deionized) water. To this solution the following were added slowly: 7.8 g of $NaHCO_3$ (after bubbling) and 2.0 g of $KHCO_3$ (after bubbling) and 0.4 g of MgO. The active agents in the mixture were solved by cautious warming. Then the mixture was cooled down and after the addition of 0.45 g of NaCl its volume was adjusted to 100 ml with deionized water.

Prior to treatment L-cysteine was added to the solution in 40 mg/ml concentration. After complete dissolution 1 ml of the solution corresponded to the planned active agent content of 1 tablet (i.e. 0.133 g L-glutamic acid, 0.066 g L-aspartic acid and 0.040 g L-cysteine) which was adjusted to the desired concentration in isotonic NaCl. In the first experiment CR was administered orally but further on we changed it for intraperitoneal treatment because of technical reasons (repeated administration to high number of animals).

The moderation of toxicity was tested in a model elaborated by us. It is suitable for the determination of changes in the biochemical parameters induced by cytostatics.

The biochemical and morphological characterization of bone marrow toxicity necessitated the study of protein and DNA content, thymidine kinase activity and changes in nucleated cell number. Intestinal damages were studied in cells isolated from the intestinal mucosa of rats treated with the test agents in vivo. Changes in the activity of disaccharidases (sucrase and maltase) and alkaline phosphatase, as markers of intestinal function, were determined. Kidney toxicity was assessed by the determination of the creatinine and urea concentrations in the serum of the treated animals.

In order to reveal the mechanism of action of Cystergin, experiments were carried out on the effect of Cystergin, as an adjuvant to Cytostatic treatment, on the glutathione reductase and glutathione-S-transferase activity.

Results:

1) Cystergin itself did not affect significantly the biochemical parameters of either the bone marrow or the intestine or the kidney.

2) When working out the optimum conditions of Cystergin administration, its reducing effect on toxicity was found to be dependent on its dose and time of administration related to the time of cytostatic treatment. Most pronounced effect of Cystergin was observed with application of 3×240 mg/kg dose i.p. (30 minutes before, simultaneously with and 30 minutes after the administration of cis-Pt).

3) Experiments aimed at reducing the toxicity of cytostatics showed that:

3.1 Cystergin treatment in a dosage schedule outlined in point 2 above, reduced the toxic side effects caused by Cisplatin. Small intestinal toxicity was reduced significantly, the seriousness of bone marrow toxicity was mitigated and the significantly elevated values of serum markers of kidney toxicity were normalized. In case of 5-FU however, the adjuvant therapy in the applied dose (3×240 mg/kg i.p.) and schedule (30 minutes before, simultaneously with and 30 minutes after the cytostatics) remained ineffective and similarly the adverse effect of CPA was only slightly modified.

3.2 In addition to mitigating the toxicity of cis-Pt, Cystergin accelerated the completion of regeneration after cytostatic treatment both in the bone marrow and intestinal mucosa.

3.3 According to the values of the dose modifying factors (bone marrow: 1.3–2.0 and intestinal mucosa: 2.5–3.1) there is a possibility, in principle, to raise the dose of cis-Pt without increasing its toxicity on the bone marrow and intestinal mucosa that would finally lead to higher antitumor activity.

4. Studies on the mechanism of action of Cystergin have revealed that decreased toxicity due to the administration of Cystergin is closely related in effect on the activity of the intestinal detoxifying enzymes.

Specific studies are set forth below wherein blood samples were obtained from the left ventricle while the animals were bled to death. Blood was centrifuged at 5000 rpm for 15 minutes at 4° C. The clinical chemical determination were made from the serum samples. Determination of glucose, urea, creatinine, cholesterol and triglyceride concentration as well as the activity of GGT, GOT, GPT and alkaline phosphatase (ALP) in the serum were made with a Beckmann-700 type analyzer. Mathematical statistical analysis was applied to evaluate the results. We used the paired "t"-test and the linear regression analysis.

This study further recognizes that the most severe side effects after a single (8 mg/kg) dose of cisplatin developed 48 hours after the treatment and further that Cystergin is most potent in reducing the side effects when administered three times i.e. 30 minutes before, simultaneously with and 30 minutes after($-30$; 0; $+30$) Cisplatin treatment.

|   | Treatment Groups: |
|---|---|
| I. = | untreated control group, 8 animals |
| II. = | 8 mg/kg Cisplatin (i.p.) + 3 × 80 mg/kg Cystergin (i.p.), ($-30$; 0; $+30$), 8 animals |
| III. = | 8 mg/kg Cisplatin (i.p.) + 3 × 160 mg/kg Cystergin (i.p.), ($-30$; 0; $+30$), 8 animals |
| IV. = | 8 mg/kg Cisplatin (i.p.) + 3 × 240 mg/kg Cystergin (i.p.), ($-30$; 0; $+30$), 8 animals |
| V. = | 8 mg/kg Cisplatin (i.p.), 8 animals |

Serum determinations were made 24 hours (Table I) and 48 hours (Table II) after the cytostatic treatment.

| Urea | $A = 610$ | $B = -78.25$ | $r = -0.7818$ |
|---|---|---|---|
| Creatinine | $A = 574$ | $B = -6.12$ | $r = -0.5284$ |
| Cholesterol | $A = 913$ | $B = -354$ | $r = -0.6311$ |
| Triglyceride | $A = 0.301$ | $B = -174$ | $r = -0.9340$ |
| GOT | $A = 783$ | $B = -6.77$ | $r = -0.9401$ |
| GPT | $A = 460$ | $B = -11.7$ | $r = -0.8945$ |
| GGT | $A = 2355$ | $B = -5.69$ | $r = -0.9431$ |
| Alkaline phosphatase | $A = 353$ | $B = -0.97$ | $r = -0.9845$ |

On the basis of experiments it can be concluded that there has been an inverse correlation between the rise in Cystergin dose and decrease in the concentration of the clinical chemical parameters and enzyme activities. Raising of the Cystergin dose resulted in decreasing urea, creatinine, cholesterol and triglyceride concentrations as well as it reduced the GGT, GOT, GPT and alkaline phosphatase activities in the serum.

b.) The paired "t" test.

Cisplatin treatment alone and in combination with smaller dose of Cystergin (groups II–III) significantly elevated the concentration of urea, creatinine, cholesterol and triglyceride and the activity of GGT, GOT, GPT and alkaline phosphatase in the serum as compared with the results of the untreated control animals.

TABLE I

THE EFFECT OF COMBINED TREATMENT WITH CISPLATIN (8 mg/kg, i.p.) and CYSTERGIN (3 × 80, 3 × 160, 3 × 240 mg/kg i.p.) ON THE CHANGE OF CLINICAL CHEMICAL PARAMETERS IN THE SERUM. (Results obtained 24 hours after Cisplatin treatment.)

| | | Experimental Groups | | | |
|---|---|---|---|---|---|
| TREATMENT | I. | II. $\bar{x} \pm SD$ | III. $\bar{x} \pm SD$ | IV. $\bar{x} \pm SD$ | V. $\bar{x} \pm SD$ |
| Cis-Pt ip. (mg/kg) + CR ip. (mg/kg) | $\bar{x} \pm SD$ Control* | 8 + 3 × 80 | 8 + 3 × 160 | 8 + 3 × 240 | 8 — |
| Parameters: | | | | | |
| glucose (a) | 7.25 ± 0.33 | 6.95 ± 0.41 | 7.34 ± 0.23 | 7.41 ± 0.21 | 7.67 ± 0.41 |
| urea (a) | 4.75 ± 0.76 | 6.35 ± 0.34 | 5.87 ± 0.49 | 5.10 ± 0.85 | 9.45 ± 0.76 |
| creatinine (b) | 65.5 ± 5.12 | 71.2 ± 4.16 | 68.8 ± 8.10 | 63.8 ± 3.21 | 146.4 ± 2.72 |
| cholesterol (a) | 1.9 ± 0.11 | 2.2 ± 0.08 | 2.2 ± 0.07 | 2.0 ± 0.13 | 2.9 ± 0.14 |
| triglyceride (a) | 0.6 ± 0.08 | 1.6 ± 0.11 | 1.4 ± 0.09 | 0.8 ± 0.10 | 1.9 ± 0.11 |
| GOT (d) | 86 ± 4.56 | 97 ± 2.31 | 90 ± 4.43 | 76 ± 3.32 | 100.7 ± 5.67 |
| GPT (d) | 18 ± 2.34 | 31 ± 1.89 | 26 ± 3.34 | 20 ± 3.45 | 45 ± 4.35 |
| GGT (d) | 29.5 ± 5.34 | 44.3 ± 6.12 | 30.7 ± 4.32 | 15.1 ± 2.38 | 61.6 ± 4.53 |
| ALP (d) | 142 ± 11.6 | 276 ± 14.8 | 200 ± 13.4 | 117 ± 16.7 | 325 ± 14.5 | a = mmol/l, b = μmol/l, c = g/l, d = U/l. $\bar{x}$ = mean, ±SD = standard deviations
*The control animals received isotonic NaCl solution in identical volume instead of cis-Pt and CR treatment.

Evaluation of Table I

Mathematical statistical analysis:

a.) Linear regression analysis. (Dose dependence study of Cystergin based on values measured in groups II, III and IV.)

The pathologically high values of clinical chemical parameters were significantly lowered by Cystergin administration as compared to the results obtained in animals treated with Cisplatin alone. The measure of decrease was most pronounced in animals given 3 × 240 mg/kg Cystergin. Changes were highly dependent on the doses applied.

TABLE II

THE EFFECT OF COMBINED TREATMENT WITH CISPLATIN (8 mg/kg, i.p.) and CYSTERGIN (3 × 80, 3 × 160, 3 × 240 mg/kg i.p.) ON THE CHANGE OF CLINICAL CHEMICAL PARAMETERS IN THE SERUM. (Results obtained 48 hours after Cisplatin treatment.)

| | | Experimental Groups | | | |
|---|---|---|---|---|---|
| TREATMENT | I. | II. $\bar{x} \pm SD$ | III. $\bar{x} \pm SD$ | IV. $\bar{x} \pm SD$ | V. $\bar{x} \pm SD$ |
| Cis-Pt ip. (mg/kg) + CR ip. (mg/kg) | $\bar{x} \pm SD$ Control* | 8 + 3 × 80 | 8 + 3 × 160 | 8 + 3 × 240 | 8 — |
| Parameters: | | | | | |
| glucose (a) | 7.34 ± 0.19 | 7.00 ± 0.33 | 6.96 ± 0.21 | 6.11 ± 0.32 | 8.38 ± 0.21 |
| urea (a) | 4.28 ± 0.69 | 7.76 ± 0.44 | 7.01 ± 0.44 | 6.06 ± 0.27 | 13.45 ± 0.43 |
| creatinine (b) | 66.8 ± 4.61 | 77.6 ± 6.16 | 71.5 ± 3.78 | 61.7 ± 5.48 | 102.7 ± 3.99 |
| cholesterol (a) | 2.01 ± 0.14 | 2.35 ± 0.21 | 2.11 ± 0.23 | 1.89 ± 0.19 | 3.05 ± 0.32 |
| triglyceride (a) | 0.68 ± 0.13 | 1.89 ± 0.16 | 1.64 ± 0.18 | 1.01 ± 0.14 | 2.26 ± 0.15 |
| GOT (d) | 82.8 ± 6.61 | 91.6 ± 4.56 | 80.1 ± 3.67 | 72.7 ± 4.35 | 115 ± 5.82 |

TABLE II-continued

THE EFFECT OF COMBINED TREATMENT WITH CISPLATIN (8 mg/kg, i.p.)
and CYSTERGIN (3 × 80, 3 × 160, 3 × 240 mg/kg i.p.) ON THE
CHANGE OF CLINICAL CHEMICAL PARAMETERS
IN THE SERUM. (Results obtained 48 hours after Cisplatin treatment.)

| TREATMENT<br>Cis-Pt ip. (mg/kg) +<br>CR ip. (mg/kg) | I.<br>$\bar{x} \pm$ SD<br>Control* | Experimental Groups | | | |
|---|---|---|---|---|---|
| | | II.<br>$\bar{x} \pm$ SD<br>8 +<br>3 × 80 | III.<br>$\bar{x} \pm$ SD<br>8 +<br>3 × 160 | IV.<br>$\bar{x} \pm$ SD<br>8 +<br>3 × 240 | V.<br>$\bar{x} \pm$ SD<br>8<br>— |
| GPT (d) | 20.5 ± 3.41 | 27.8 ± 2.35 | 20.1 ± 3.45 | 18.5 ± 4.52 | 46 ± 5.12 |
| GGT (d) | 27.8 ± 6.34 | 40.7 ± 6.66 | 26.9 ± 4.35 | 12.6 ± 4.82 | 64 ± 4.98 |
| ALP (d) | 147 ± 6.78 | 260 ± 7.59 | 160 ± 8.76 | 107 ± 7.76 | 343 ± 10.8 | a = mmol/l, b = μmol/l, c = g/l, d = U/l. $\bar{x}$ = mean, ±SD = standard deviations
*The control animals received isotonic NaCl solution in identical volume instead of cis-Pt and CR treatment.

Mathematical statistical analysis:
a.) Linear regression analysis. (Dose dependence study of intraperitoneally administered Cystergin based on values obtained in groups II, III and IV.)

| Urea | A = 634 | B = −68.4 | r = −0.8702 |
| Creatinine | A = 707 | B = −5.83 | r = −0.7204 |
| Cholesterol | A = 194 | B = −15 | r = −0.061 |
| Triglyceride | A = 276 | B = −97.8 | r = −0.8076 |
| GOT | A = 750 | B = −6.72 | r = −0.9136 |
| GPT | A = 347 | B = −6.63 | r = −0.9329 |
| GGT | A = 320 | B = −5.88 | r = −0.9197 |
| Alkaline phosphatase | A = 449 | B = −1.75 | r = −0.9139 |

Results show an inverse correlation between the rise in Cystergin dose and decrease in the concentration of the clinical chemical parameters and enzyme activities (negative correlation). Raising of the Cystergin dose results in a linear fall of the concentration of urea, creatinine, cholesterol and triglyceride concentration as well as in a decrease of GGT, GOT, GPT and alkaline phosphatase activity in the serum.

b.) The paired "t" test

Cisplatin by itself (group V) and Cisplatin+Cystergin treatment (groups II–III) significantly increased the concentration of urea, creatinine, cholesterol and triglyceride as well as the activity of GGT, GOT and GPT and alkaline phosphatase in the serum as compared to the results obtained in untreated controls.

Comparison of the values of the untreated controls and those of animals in group IV treated with the combination of 3×240 mg/kg Cystergin and 8 mg/kg Cisplatin makes it clear that Cystergin was able to normalize the pathologically high concentration and activity values if administered in 3×240 mg/kg doses.

Clinical chemical parameters of animals treated with Cisplatin combined with Cystergin were significantly lower than those of animals treated with Cisplatin alone. Decrease and normalization of the parameters were in correlation with the Cystergin dose applied.

These studies indicate that Cisplatin in the 8 mg/kg dose resulted in a significant rise in serum urea, creatinine, cholesterol and triglyceride concentration as well as in GGT, GOT, GPT and alkaline phosphatase activity compared to those of the untreated controls.

The pathologically high values of the above parameters were reduced by Cystergin in a dose dependent manner. Except carbamide and triglyceride concentrations all parameters reached the values found in the untreated controls.

Increased serum urea and creatinine levels are considered as indicators of nephrotoxicity, therefore it can be concluded that Cisplatin treatment in itself caused disturbances in renal functions. Cystergin administered, in adequate doses is able to moderate the renal toxicity of Cisplatin. The simultaneous rise of serum GGT, GOT and GPT activities are reliable diagnostic signs of disturbed hepatic functions. These toxic effects of the cisplatin, however, are moderated by Cystergin in a dose dependent fashion.

Increased cholesterol and triglyceride levels indicate disorders in the equilibrium of intermediary metabolism; since under unchanged dietary conditions the endogenous lipid mobilization is likely to have set off.

Cystergin moderates the rise of cholesterol and triglyceride levels induced by Cisplatin, though the measure of mitigation in case of triglyceride is less pronounced.

Elevated alkaline phosphatase activity suggests hepatobiliary disturbances, disorders in Ca homeostasis and damages to the intestinal mucosa. Cisplatin in itself increases the alkaline phosphatase activity that can be mitigated by adequate doses of Cystergin.

In view of our results Cystergin seems to be a potent agent in moderating or even in eliminating the harmful effects of Cisplatin on the kidneys, liver and intestinal mucosa.

What is claimed is:

1. A method of alleviating toxicity originating from treatment with anticancer platinum compound(s), comprising administering an effective amount of the amino acids L-glutamic acid, L-aspartic acid and L-cysteine to a patient subject to the treatment with the anticancer compound(s).

2. The method according to claim 1 wherein the amino acids are present in a pharmaceutical composition in the following molar ratios:

| L-glutamic acid: | L-cysteine from 4:1 to 1:1 |
| L-aspartic acid: | L-cysteine from 2:1 to 1:2 |
| L-glutamic acid: | L-aspartic acid from 3:1 to 1:3. |

3. The method according to claim 1 wherein the amino acids are administered contemporaneously and in connection with the anticancer platinum compound(s).

4. The method according to claim 1 wherein the anticancer compound is cisplatin, carboplatin or iproplatin.

5. The method of claim 1 wherein the amino acids are present in the following amounts (w/w):

| 50–60% | L-glutamic acid |
| 25–30% | L-aspartic acid |
| 15–20% | L-cysteine. |

6. The method of claim 2 wherein the pharmaceutical composition is administered in tablet form.

7. A method of (i) increasing the regeneration of bone marrow or intestinal mucosa in a patient whose bone marrow or intestinal mucosa has been damaged or (ii) reducing renal or liver toxicity caused by the administration of an anti-cancer platinum compound, wherein the method comprises subjecting to the patient a therapeutically effective amount of a pharmaceutical composition comprising L-glutamic acid, L-aspartic acid and L-cysteine having the following molar ratios:

| | |
|---|---|
| L-glutamic acid: | L-cysteine from 4:1 to 1:1 |
| L-aspartic acid: | L-cysteine from 2:1 to 1:2 |
| L-glutamic acid: | L-aspartic acid from 3:1 to 1:3. |

8. The method according claim 7 wherein the amino acids are administered contemporaneously and in connection with the anticancer platinum compound(s).

9. The method according to claim 7 wherein the anticancer compound is cisplatin, carboplatin or iproplatin.

10. The method according to claim 7 wherein the pharmaceutical composition is in the form of a tablet for oral administration.

11. The method according to claim 8 wherein the amino acids are present in the following amounts (w/w):

| | |
|---|---|
| 50–60% | L-glutamic acid |
| 25–30% | L-aspartic acid |
| 15–20% | L-cysteine. |

* * * * *